United States Patent [19]

Dessau

[11] 4,423,280

[45] Dec. 27, 1983

[54] SELECTIVE SORPTION BY ZEOLITES

[75] Inventor: Ralph M. Dessau, Edison, N.J.

[73] Assignee: Mobil Oil Corporation, New York, N.Y.

[21] Appl. No.: 307,050

[22] Filed: Sep. 30, 1981

Related U.S. Application Data

[63] Continuation-in-part of Ser. No. 105,190, Dec. 19, 1979, Pat. No. 4,309,281.

[51] Int. Cl.³ ............................................. C07C 7/13
[52] U.S. Cl. ................................ 585/829; 208/310 Z; 585/820
[58] Field of Search .................... 208/310 Z; 585/820, 585/827, 829; 210/690; 55/75

[56] References Cited

U.S. PATENT DOCUMENTS

| | | | |
|---|---|---|---|
| 3,485,748 | 12/1969 | Eberly et al. | 208/310 R |
| 3,699,182 | 10/1972 | Cattanach | 585/831 |
| 3,702,886 | 11/1972 | Argauer et al. | 423/328 |
| 3,732,326 | 5/1973 | Chen | 208/310 Z |
| 4,016,245 | 4/1977 | Plank et al. | 423/328 |
| 4,076,842 | 2/1978 | Plank et al. | 423/328 |

*Primary Examiner*—G. L. Kaplan
*Assistant Examiner*—William Leader
*Attorney, Agent, or Firm*—Michael G. Gilman; Charles J. Speciale; L. G. Wise

[57] ABSTRACT

An improved hydrocarbon separation process by the selective sorption properties of certain members of a novel class of zeolites is provided. The novel class of zeolites is characterized by a silica to alumina mole ratio greater than 12 and a Constraint Index within the approximate range of greater than about 2 to about 12. The process of this invention involves selective separation of non-aromatic compounds in admixture with aromatic compounds by contacting the mixture with zeolite ZSM-5, ZSM-11, ZSM-23 or ZSM-35, said zeolite having a $SiO_2/Al_2O_3$ mole ratio of at least about 12, to effect the selective sorption of said non-aromatic compounds by said zeolite.

15 Claims, No Drawings

SELECTIVE SORPTION BY ZEOLITES

CROSS-REFERENCE TO RELATED APPLICATION

This is a continuation-in-part of application Ser. No. 105,190, filed Dec. 19, 1979, now U.S. Pat. No. 4,309,281.

BACKGROUND OF THE INVENTION

1. Field of the Invention

This invention relates to an adsorptive hydrocarbon separation process using crystalline zeolites. More specifically, the invention pertains to the selective separation of non-aromatic compounds in admixture with aromatic compounds over a particular crystalline zeolite which selectively sorbs the non-aromatic compounds from the mixture. The zeolites found to be useful in the present process are those having a silica/alumina mole ratio of greater than about 12, a Constraint Index of between about greater than 2 and about 12, and in particular zeolites ZSM-23 and ZSM-35.

2. Description of the Prior Art

It has long been known that certain porous substances such as silica gel, activated char, and zeolites, have certain selective adsorption characteristics useful in resolving a hydrocarbon mixture into its component parts. Thus, silica gel is selective in removing aromatic hydrocarbons from non-aromatic hydrocarbons and activated chars are useful in separating olefins from mixtures with paraffins. Similarly, it is well known in the art that certain crystalline zeolites can be used to separate certain hydrocarbons from feed mixtures.

The selective sorption properties of zeolites are generally known and have been described, for instance, in U.S. Pat. Nos. 2,850,549; 2,866,835; 3,037,338 and 3,218,367. The general sorption properties of zeolites have been disclosed in some of the earlier patents on the zeolites per se, namely U.S. Pat. Nos. 2,882,243 and 2,882,244. Additionally, there are numerous literature references, especially those of Barrer, which deal extensively with the sorption properties of crystalline zeolites. Generally speaking, crystalline zeolites are shape-selective in that they will admit molecules of specific geometry while excluding other molecules.

The separation of normal paraffins from branched chained paraffins for example can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules. U.S. Pat. Nos. 3,265,750 and 3,510,423 for example, disclose processes in which larger pore diameter zeolites such as the type X or type Y structured zeolites can be used to separate olefinic hydrocarbons from non-olefinic hydrocarbons. Processes to separate straight chain hydrocarbons from a mixture of straight chain and non-straight chain hydrocarbons using a molecular sieve selective adsorbent are described in U.S. Pat. Nos. 3,619,409 and 3,619,416.

Additionally, such crystalline zeolites will exclude aromatics such as benzene while admitting normal hexane. It has been disclosed in British Pat. No. 600,453 that zeolites can be employed as selective sorption agents and that such zeolites will sorb polar molecules in preference to less polar molecules. A method for selectively sorbing a compound of low polarity in admixture with a compound of greater polarity using a zeolite is disclosed in U.S. Pat. No. 3,732,326. The latter patent discloses use of zeolite ZSM-5 for selectively sorbing hydrocarbons of low polarity in admixture with compounds of greater polarity such as water, alcohols, acids, aldehydes and halogen-substituted compounds.

U.S. Pat. No. 3,723,302 discloses a process for separating olefins from a feed stream containing olefins and paraffins using type X or type Y zeolites. A process for the separation of olefins from a hydrocarbon feed mixture using a zeolite absorbent is disclosed in U.S. Pat. No. 3,969,223. A process for the separation and recovery of hydrocarbons selected from paraffins or olefins or both from admixture with aromatic hydrocarbons using aluminum-deficient mordenite is disclosed in U.S. Pat. No. 3,485,748.

The separation of xylene isomers has received a great deal of attention. This interest is generally attributed to the usefulness of para-xylene in the manufacture of terephthalic acid which is an intermediate in the manufacture of synthetic fibers such as "Dacron," "Mylar" and "Terylene." Mixtures of xylene isomers generally contain a concentration of about 24 weight percent para-xylene in the equilibrium mixture. Processes to separate xylene isomers include low temperature crystallization, fractional distillation, selective sulfonation with subsequent hydrolysis and selective solvent separation. Such processes, however, have involved high operation costs and usually result in a limited yield.

U.S. Pat. No. 3,868,429 discloses a method to separate xylene isomers by using activated carbon.

The separation of xylene isomers by the use of faujasite zeolites (type X and type Y zeolites) has been extensively studied. The use of type X and type Y zeolites in xylene isomer separation and similar separations is disclosed in U.S. Pat. Nos. 3,114,782; 3,126,425; 3,133,126; 3,558,730; 3,558,732; 3,626,020; 3,663,638; 3,665,046; 3,686,342; 3,943,183 and 4,051,192.

U.S. Pat. No. 3,793,385 discloses a process for the separation of aromatic isomers, more particularly xylene isomers, by using zeolite beta.

U.S. Pat. No. 3,724,170 discloses chromatographic separation of $C_8$ aromatic mixtures over zeolite ZSM-5. U.S. Pat. No. 3,699,182 discloses use of zeolite ZSM-5 in a process for selective separation of biphenyls from mixtures containing same and para-disubstituted aromatic isomers from mixtures containing same. British Pat. No. 1,420,796 shows use of zeolite ZSM-5 for adsorptive separation of p-xylene and ethylbenzene from a mixture comprised of the xylene isomers and ethylbenzene.

Catalytic dewaxing of gas oil fractions over the shape selective zeolites ZSM-5, ZSM-11, ZSM-12, ZSM-35 and ZSM-38 is taught in U.S. Pat. Nos. 3,980,550 and 4,149,960.

The ZSM-5 class of crystalline zeolites has been shown to be catalytically selective. This shape selectivity can be further enhanced by the use of very large crystals, impregnation with Mg and P to reduce zeolite pore openings and coke selectivation. These modified zeolite catalysts have been very effective in such reactions as selective toluene disproportionation which yields predominantly paraxylene as the product and toluene-ethylene alkylation yielding primarily para-ethyltoluene.

Zeolite ZSM-5 possesses pore openings intermediate in size between the small pore and the large pore zeolites. It sorbs at room temperature straight chain mono-methyl-substituted paraffins and monocyclic hydrocarbons at significantly faster rates than those containing dimethyl-substituted or quaternary carbon atoms, and it excludes molecules with critical dimensions larger than that of 1,3,5-trimethylbenzene. Zeolite ZSM-5 has a pore system which differentiates catalytically molecules having a straight chain, a methyl substitution and a dimethyl substitution. The catalytic properties of ZSM-5 are further elucidated by Chen and Garwood in *Some Catalytic Properties of ZSM-5, a New Shape Selective Zeolite*, JOURNAL OF CATALYSIS, Vol. 52, No. 3 (May 1978).

Satterfield and Cheng, *Liquid Sorption Equilibrium of Selected Binary Hydrocarbon Systems in Type Y Zeolites*, AICHE JOURNAL, Vol. 18, No. 4, p. 720, July 1972 and Satterfield and Smeets, *Liquid Sorption Equilibria of Selected Binary Paraffin Systems in NaY Zeolite*, AICHE JOURNAL, Vol. 20, No. 3, p. 618, May 1974, teach that on zeolite Y aromatic compounds are selectively adsorbed over paraffins and smaller compounds are adsorbed in preference to larger compounds. Contrary to said teaching, the zeolites for use in the instant invention yield the unexpected results of selective adsorption of paraffins over aromatics and selective adsorption of higher molecular weight molecules over smaller members of the same family.

SUMMARY OF THE INVENTION

In accordance with the present invention, there has now been discovered an improved hydrocarbon separation process accomplished by the selective sorption properties of certain zeolites within a novel class. The zeolites useful in this invention are characterized by a silica to alumina mole ratio of at least 12 and a Constraint Index within the approximate range of greater than 2 to about 12. In particular, said zeolites include ZSM-23 and ZSM-35.

DESCRIPTION OF SPECIFIC EMBODIMENTS

The process of this invention is concerned with the separation of hydrocarbon mixtures by the selective sorption properties of certain zeolites within a novel class of zeolites. The novel class of zeolites is characterized by a silica to alumina mole ratio of at least 12 and a Constraint Index within the approximate range of greater than 2 to about 12. Zeolites useful herein are ZSM-23 and ZSM-35.

The zeolites useful herein possess the ability to selectively sorb non-aromatic compounds such as, for example, linear paraffins, linear olefins, methyl-branched paraffins and methyl-branched olefins, from mixtures thereof with aromatic compounds, such as, for example, benzene and alkyl-substituted benzene, e.g., toluene, xylenes, ethylbenzene, etc.

A limiting factor on which compounds will be sorbed to any extent, either selectively from a mixture or individually, by the zeolites for use herein in the critical dimension of the compound. For the zeolites herein utilized, the compounds must have a critical dimension of 6.8 Angstrom units or less to be sorbed. Therefore, to benefit from the selective sorption process herein claimed, both or all components of the mixture will have a critical dimension of 6.8 Angstroms or less.

Utilizing the zeolites of the present invention with crude oils, heavy oils and lube base stocks can be quite useful in the dewaxing of such oils via the selective sorption and separation of paraffins. Thus paraffins can be selectively removed to such an extent so as to reduce the pour point of the oil, i.e. increase its fluidity. The mixture of non-aromatic and aromatic compounds may also be reformate or BTX-type feedstocks where adsorptive upgrading thereof will be accomplished by the present process. For example, a reformate will be upgraded to a higher octane number by the present process with selective removal of paraffins. In this regard, the present method is valuable when compared to cracking out unwanted paraffins since the sorptively separated hydrocarbons may be recovered and thereafter utilized.

In adsorptive separation processes, an important factor that is used to determine the ability of a particular adsorbent to separate components of a feed mixture is the selectivity of the adsorbent for one component as compared to another component. The selectivity, as used throughout this specification, is defined as the ratio of the two components of the adsorbed or retained phase over the ratio of the same two components in the unadsorbed phase at equilibrium conditions. Selectivity is derived as follows:

$$\text{Selectivity} = S_{A,B} = \frac{(A \text{ adsorbed on zeolite})}{(B \text{ in solution})} \times \frac{(B \text{ adsorbed on zeolite})}{(A \text{ in solution})}$$

where A and B are the two components of the feed represented in volume percentages.

The equilibrium conditions as defined herein are determined when the feed is contacted with a bed of adsorbent and no change in composition results after such contacting. In other words, there is no net transfer of material occurring between the unadsorbed and adsorbed phases.

As can be seen, where the selectivity of the two components approaches unity, there is no preferential adsorption of one component by the adsorbent because the ratio of the feed to the components in the adsorbed and unabsorbed phases is equal. As the value of $S_{A,B}$ becomes less or greater than unity, there is a preferential selectivity by the adsorbent for one of the two components. When comparing a selectivity of component A over component B, an $S_{A,B}$ larger than unity indicates preferential adsorption of component A within the adsorbent, while an $S_{A,B}$ less than unity would indicate that component B is preferentially adsorbed by the adsorbent.

The novel process of the instant invention involves contacting a mixture, existing either as a gas, liquid or mixed phase with a member of the class of zeolites of this invention for a period of time to selectively sorb a preferred compound within the internal pore structure of said zeolite. The components of the mixture that are not sorbed are thus carried off. The compound sorbed is thereafter recovered from the internal pore structure of the zeolite by conventional desorbing techniques such as stripping. Although inert solvents were employed in static batch systems to carry out many of the experiments illustrating this invention, the novel process of this invention can also be conducted in flow type (continuous) systems, e.g. continuous chromatographic type operation. In such a flow type system, a mixture is passed through a bed containing a member of the class of zeolites of the present invention. The preferred compound is adsorbed or retained in the bed, while the unadsorbed compound is removed. The processes of this invention can be conducted in the presence of polar, e.g. water or alcohol, or non-polar solvents. Thus, selective sorptions of the kind and type described herein can take place in the presence of water, i.e. in aqueous solution.

The temperature at which the novel process of this invention is conducted is not considered critical, so long as it is maintained below that required for chemical reaction to occur, e.g. below cracking temperature. The temperature should thus be maintained below about 150° C., when an acidic zeolite is used (e.g. a zeolite having an Alpha value greater than 10). When a relatively non-acidic zeolite, e.g. one having a $SiO_2/Al_2O_3$ mole ratio of about 1000 or more, for instance, is used or when the zeolite has been converted to the alkali metal-containing form by ion exchange, for example, then higher temperatures, such as up to about 400° C. may be used. Preferably, the processes of this invention can be conducted in the temperature range between ambient and about 150° C.

Obtaining even higher selectivities for the zeolites for this improved process can be accomplished by reducing the diffusional rate characterics of these zeolites. The diffusional rate characteristic is defined as the rate of which a zeolite, or other adsorbent, sorbs a particular hydrocarbon, e.g. hexane or o-xylene. Modification of the diffusional rate characteristics may be suitably effected by precoking. Another means of achieving desired lower diffusional rate characteristics is the use of large crystal size zeolite having a minimum crystal dimension of greater than about 0.5 micron. Generally, the crystal size should be in the approximate range of between about 0.5 micron and greater than about 250 microns, and preferably in the range of between about 0.5 micron and 250 microns. As used throughout this specification and claims, zeolites with crystal diameters of about 0.02 micron to about 0.5 micron will be designated as "small crystal size" and zeolites with crystal diameters greater than about 0.5 micron will be designated as "large crystal size."

Still another means of achieving desired lower diffusional rate characteristics is to incorporate, such as by cation exchange, bulky cations such as cesium or tetramethylammonium cations with the useful zeolites of this invention. Other cations which may be exchanged into the zeolite to affect lower diffusional rate characteristics and thereby increase selectivity thereof for the present process include $Na^+$, $H^+$, $Cu^{++}$, $K^+$, $Sr^{++}$ and similar cations. A correlation of sorption selectivity exhibited by the exchanged zeolite for use herein with the ionic radius of the cation involved may be demonstrated.

Silica/alumina mole ratio also has an effect on the sorption selectivity of the zeolites for use herein, especially where large polarity differences are involved. Thus, for example, H-ZSM-5 having a $SiO_2/Al_2O_3$ mole ratio of 1670 may have a selectivity from four to five times that of a H-ZSM-5 having a $SiO_2/Al_2O_3$ mole ratio of 75. Likewise, it has been found that steaming a zeolite useful herein will also increase selectivity thereof. For example, an unsteamed H-ZSM-5 may provide a selectivity factor of 3.2, while that same zeolite after having been steamed for 2 hours at 538° C. will provide a selectivity of as much as 7.3.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, or course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is valuable in some instances to use zeolites having much higher silica to alumina mole ratios, e.g. 1600 and above. In addition, zeolites as otherwise characterized herein but which are substantially free of aluminum, i.e. having silica to alumina mole ratios up to and including infinity, are found to be useful and even preferable in some instances. Such "high silica" or "highly siliceous" zeolites are intended to be included within this description. Also to be included in this definition are the pure silica analogs of the useful zeolites of this invention, i.e. having absolutely no aluminum (silica to alumina mole ratio of infinity). Thus, zeolites useful herein have silica to alumina mole ratios of between about 12 and infinity, preferably greater than about 200, more preferably greater than about 500 and even more preferably greater than about 1000.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules, i.e. those having a critical dimension of greater than 6.8 Angstrom Units. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

There also may be instances where the activity is so low (i.e. silica to alumina mole ratio approaching infinity) that the constraint index cannot be adequately measured, if at all. In such situations, Constraint Index is meant to mean the Constraint Index of the exact same substance (i.e. same crystal structure as determined by such means as x-ray diffraction pattern) but in a measureable form (i.e. aluminum containing form).

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Constraint Index values for some typical materials are:

| | CONSTRAINT INDEX |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of greater than about 2 to about 12 for the Constraint Index of a particular zeolite. Such a zeolite exhibits the constrained access as herein defined and is to be regarded as having a Constraint Index in the range of greater than about 2 to about 12. Also contemplated herein as having a Constraint Index in the range of greater than about 2 to about 12 and therefore within the scope of the defined novel class of highly siliceous zeolites are those zeolites which, when tested under two or more sets of conditions within the above-specified ranges of temperature and conversion, produce a value of the Constraint Index slightly less than 2, e.g. 1.9, or somewhat greater than 12, e.g. 14 or 15, with at least one other value within the range of greater than about 2 to about 12. Thus, it should be understood that the Constraint Index value as used herein is an inclusive rather than an exclusive value. That is, a crystalline zeolite when identified by any combination of conditions within the testing definition set forth herein as having a Constraint Index in the range of greater than about 2 to 12 is intended to be included in the instant novel zeolite definition whether or not the same identical zeolite, when tested under other of the defined conditions, may give a Constraint Index value outside of the range of greater than about 2 to about 12.

The novel class of zeolites defined for use herein is exemplified by ZSM-23 and ZSM-35.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint," which establishes the identity of the specific crystalline zeolite material.

The specific zeolites described, when prepared in the presence of organic cations, are unsuitable for use herein, possibly because the intra-crystalline free space is occupied by organic cations from the forming solution. They may be made suitable by calcination in an inert atmosphere, such as, for example, at about 538° C. for from about one hour to about 5 hours in a nitrogen or air atmosphere. If desired these zeolites may be base exchanged with suitable compounds, e.g. salts, to get desired cationic form, e.g. sodium, hydrogen, ammonium, etc. The presence of organic cations in the forming solution may not be absolutely essential to the formation of this type zeolite; however, the presence of these cations does appear to favor the formation of this special class of zeolite.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-23 and ZSM-35.

In a preferred aspect of this invention, the zeolites hereof are selected as those providing, among other things, a crystal framework density in the dry hydrogen form of not less than about 1.6 grams per cubic centimeter. It has been found that zeolites which satisfy all three of the discussed criteria are most desired for several reasons. Therefore, the preferred zeolites useful with respect to this invention are those having a Constraint Index as defined above of greater than about 2 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusal sustained activity and stability of this special class of zeolites is associated with its high crystal anionic framework density of not less than about 1.6 grams per cubic centimeter. This high density must necessarily be associated with a relatively small mount of free space within the crystal, which might be expected to result in more stable structures. This free space, however, is important as the focus of catalytic activity.

Crystal framework densitites of some typical zeolites, including some which are not within the purview of this invention are:

|  | Void Volume | Framework Density |
| --- | --- | --- |
| Ferrierite | 0.28 cc/cc | 1.76 g/cc |
| Mordenite | .28 | 1.7 |
| ZSM-5, 11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

The following examples will serve to illustrate the process of the invention without limiting same.

EXAMPLE 1

This example illustrates the preparation of small crystal size ZSM-5.

An organic salt solution was prepared by mixing 1.6 parts of n-propyl bromide, 1.9 parts of tri-n-propylamine, 3.1 parts of methyl ethyl ketone and 10.4 parts of water. The mixture was reacted at about 100° C. for about 14 hours. The aqueous phase of the reacted mixture is designated Solution A.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W. R. Grace). The solution was cooled to approximately 15° C.

An acid solution was prepared by adding 1 part aluminum sulfate (17.2 wt % $Al_2O_3$) to 16.4 parts water followed by 2.4 parts NaCl and 2.9 parts of Solution A.

These solutions were mixed in an agitated vessel while 3.9 parts of NaCl were added. The gel molar ratios expressed as oxides are the following.

$SiO_2/Al_2O_3 = 78.4$
$Na_2O/Al_2O_3 = 49.9$

The gel was agitated for 4 hours at ambient temperature then heated to 95°–110° C. and held for 40 hours with severe agitation. When approximately 65% of the gel was crystallized, the temperature was increased to 150°–160° C. and held there until crystallization was complete.

The zeolite slurry product was diluted with 4–5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the sodium level of the zeolite was less than 1.0 wt %. The washed zeolite was then filtered, dried and identified as ZSM-5 having a silica/alumina mole ratio of at least 12; i.e., about 70, and a Constraint Index of about 8.3.

The dried zeolite product was calcined in flowing $N_2$ for 3 hours at 538° C. than ion exchanged twice with 1 N $NH_4NO_3$ solution (5 parts $NH_4NO_3$ solution/1 part zeolite) for 1 hour at ambient temperature and dried at about 120° C. to arrive at a $NH_4$-ZSM-5 zeolite.

EXAMPLE 2

The preparation of the acid form (HZSM-5) of the small crystal size $NH_4$-ZSM-5 of Example 1 was conducted via the programmed calcination of the $NH_4$-ZSM-5 of Example 1 with air in a furnace at the approximate range of about 1.1° C./minute until a temperature of 537.8° C. was obtained and maintained at that temperature for 5 hours.

EXAMPLE 3

This example illustrates the preparation of large crystal size ZSM-5.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W. R. Grace). The solution was cooled to approximately 15° C.

An acid solution was prepared by adding 1 part aluminum sulfate (17.2 wt % $Al_2O_3$) to 16.4 parts water followed by 2.4 parts sulfuric acid (93 wt % $H_2SO_4$) and 1.2 parts NaCl.

These solutions were mixed in an agitated vessel while 3.9 parts of NaCl were added. The gel molar ratios expressed as oxides are the following:

$SiO_2/Al_2O_3 = 78.4$
$Na_2O/Al_2O_3 = 49.9$

An organic solution was prepared by adding 1.6 parts n-propyl bromide and 3.1 parts methyl ethyl ketone to 1.9 parts tri-n-propylamine and added to the gel.

The mixture was reacted at 65.5°–71.1° C. with severe agitation for 29 hours.

The zeolite slurry product was diluted with 4–5 parts water per part slurry and 0.002 parts of flocculent (Rohm & Haas Primafloc C-7) per part slurry, allowed to settle and supernatant liquid was drawn off. The settled solids were reslurried to the original volume of the preceding step with water and 0.0005 parts of flocculent per part slurry. After settling, the aqueous phase was decanted. This procedure was repeated until the decant supernatant liquid was Cl-free. The washed zeolite was then filtered, dried and identified as ZSM-5 having a silica/alumina mole ratio of at least 12; i.e., about 70, and a Constraint Index of about 8.3.

The dried zeolite product was calcined in flowing $N_2$ for 3 hours at 538° C. then ion exchanged twice with 1 N $NH_4NO_3$ solution (5 parts $NH_4NO_3$ solution/1 part zeolite) for 1 hour at ambient temperature and dried at about 120° C. to arrive at a $NH_4$-ZSM-5 zeolite.

EXAMPLE 4

The preparation of the acid form (HZSM-5) of the large crystal size $NH_4$-ZSM-5 of Example 3 was conducted via the programmed calcination of $NH_4$-ZSM-5 of Example 3 with air in a furnace at the rate of about 1.1° C./minute until a temperature of 537.8° C. was attained and maintained at that temperature for 5 hours.

EXAMPLE 5

This example illustrates the preparation of small crystal size ZSM-11.

A sodium silicate solution was prepared by mixing 16.8 parts water, 28.9 parts sodium silicate (28.7 wt % $SiO_2$, 8.9 wt % $Na_2O$, 62.4 wt % $H_2O$) 0.05 parts 50% wt NaOH and 0.08 parts Daxad 27 (W. R. Grace).

An acid solution was prepared by adding 1 part aluminum sulfate (17.2% wt $Al_2O_3$) to 12.6 parts $H_2O$ and then adding 2.9 parts $H_2SO_4$ and 1.7 parts NaCl.

These solutions were mixed in an agitated vessel and 1.2 parts NaCl and 0.8 parts $H_2O$ were added to the gel.

An organic solution containing 2.9 parts tetrabutylammonium bromide and 4.2 parts water was then added to the gel and thoroughly blended.

The mixture was heated to 93.3° C. and held for 234 hours with a high level of agitation. At the end of this period the temperature was raised to 137.8° C. for 72 hours to complete crystallization.

The crystallized product was washed and dried and then identified as 105% crystallinity ZSM-11 by X-ray diffraction with the following chemical analysis:

|  | % wt. |
| --- | --- |
| $Al_2O_3$ | 1.99 |
| $SiO_2$ | 92.0 |
| Na | 0.60 |
| N | 0.65 |
| C | 9.95 |

The washed and dried zeolite product was calcined in flowing $N_2$ for 3 hours at 537.8° C. then ion exchanged with 1 N $NH_4NO_3$ solution (5 parts $NH_4NO_3$ solution/1 part zeolite) for 1 hour at ambient temperature and dried at about 121° C.

The silica to alumina mole ratio of the resultant zeolite was 78.

EXAMPLE 6

This example illustrates the preparation of small crystal size zeolite $NH_4$-ZSM-12.

A reaction mixture was prepared by mixing 65 parts of Hi-Sil (a precipitated $SiO_2$), 6.3 parts NaOH, 1 part $Al(NO_3)_3$ $9H_2O$, 40 parts tetraethylammonium bromide and 310 parts $H_2O$. The mixture was changed to a vessel, thoroughly agitated and heated to about 160° C. and held for about 16 hours with agitaton. At this point the reaction mixture was cooled and 1.1 parts of NaAlO₂ and 2.7 parts H₂O were added. The reaction mixture was reheated to 160° C. and held for an additional 24 hours at 160° C. with agitation to complete crystallization.

The crystallized product was washed and dried and then identified as 90% ZSM-12 by X-ray diffraction with the following chemical analysis:

|  | % wt |
|---|---|
| Al₂O₃ | 1.79 |
| SiO₂ | 95.1 |
| Na | 0.34 |
| N | 0.98 |
| C | 7.63 |

The washed and dried zeolite was calcined in flowing N₂ for 3 hours at 537.8° C. then ion exchanged three times with 1 N NH₄NO₃ solution (5 parts NH₄NO₃ solution/1 part zeolite) for 1 hour at ambient temperature and dried at about 121° C. to finally obtain a NH₄-ZSM-12 zeolite.

The silica to alumina mole ratio of the resultant zeolite was 95.

EXAMPLE 7

The preparation of HZSM-12 from the NH₄-ZSM-12 of Example 6 was conducted via the programmed calcination of NH₄-ZSM-12 with air in a furnace at the rate of about 1.1° C./minute until a temperature of 537.8° C. was attained and maintained at that temperature for 5 hours.

EXAMPLE 8

Small crystal size CS-ZSM-5 was prepared by the ion-exchange of NH₄-ZSM-5 of Example 1 with a cesium chloride solution containing a small amount of cesium hydroxide, resulting in an ammonium removal of approximately 99%.

EXAMPLE 9

This example illustrates the preparation of a highly siliceous ZSM-5 zeolite with a silica to alumina mole ratio of about 1600 to 1.

Prereacted organics preparation

The following materials were charged to an autoclave: 0.30 parts methylethyl ketone, 0.18 parts tri-n-propylamine and 0.15 parts n-propyl bromide. The contents were mixed with gentle agitation for 15 minutes. The agitation was stopped and 1 part water was charged to the autoclave. The autoclave was sealed and heated to 104.4° C. and held at 104.4° C. for 15 hours. After this reaction period the temperature was raised to 160° C. and the unreacted organics were flashed off. The aqueous phase was removed containing the prereacted organics and contained 1.44% wt. nitrogen.

| Zeolite Synthesis Solution Preparation | |
|---|---|
| Silicate Solution | |
| 1 part | Q-brand sodium silicate |
| 0.58 parts | H₂O |
| 0.0029 parts | Daxad 27 |
| Acid Solution | |
| 0.10 parts | H₂SO₄ |
| 0.045 parts | NaCl |
| 0.56 parts | prereacted organics |
| 0.16 parts | H₂O |
| Additional Solids | |
| 0.14 parts | NaCl |
| Additional Liquid | |
| 0.029 parts | H₂O |

Procedure

The silicate solution and acid solution were mixed in a mixing nozzle to form a gel which was discharged into an autoclave to which 0.029 parts water had been previously added. The gel was whipped by agitation and 0.14 parts NaCl were added and thoroughly blended. The autoclave was sealed and heated to about 104.4° C. with agitation at 90 rpm and held for 54.3 hours until crystallization was complete. The contents of the autoclave were cooled and discharged. The crystallized product was analyzed by x-ray diffraction and was found to be 100 weight percent ZSM-5. The chemical analsysis of the thoroughly washed crystalline product was as follows:

|  | % wt | Mole Ratio |
|---|---|---|
| Al₂O₃ | 0.10 | 1.0 |
| SiO₂ | 98.3 | 1670 |
| Na | 1.6 | — |
| Na₂O | — | 35.5 |
| N | 0.75 | 63.9 |
| C | 8.98 | 892 |

EXAMPLES 10 TO 25

Due to the high hydrophobicity of all zeolites used, no pretreatment to remove sorbed water was required prior to their use in the sorption experiments.

In order to develop a meaningful diagnostic evaluation of zeolites that could be used for predicting separation properties, the selective sorption properties of various zeolites under competitive conditions were examined. In general, two or more substrates were dissolved in an inert (non-sorbable) solvent and the relative decrease in concentration of each sorbate due to addition of various zeolites was measured.

The sorbates used were purest forms available commercially. The three inert non-sorbable solvents, i.e. those having a critical dimension of greater than 6.8 Angstrom Units used were:

1,3,5-trimethylbenzene (mesitylene) from Aldrich, hereinafter designated as M, 1,3,5-triisopropylbenzene from Chem Samples, hereinafter designated as T, and 1,3-di(trifluoromethyl)benzene from PCR Research Chem, hereinafter designated as D.

In a typical experiment, 2 grams of a solution containing two sorbates (2.5% by weight each) in an inert solvent was added directly to 1 gram of a zeolite contained in a vial. This mixture, which occasionally was shaken or stirred at room temperature, was sampled periodically for changes in substrate concentrations. These samples were analyzed by vapor phase chromatography and were compared to the original solution analyzed in the identical manner. The selectivity was calculated by the formula defined herein.

Examples 10 to 25 serve to illustrate the selective separation of a non-aromatic compound, i.e. a paraffin (n-nonane), from an aromatic compound (para-xylene) in admixture therewith.

In each of Examples 10 to 12, the zeolite employed was prepared by the general procedure of Example 2. The zeolites of Examples 13 and 14 were prepared by the general procedure of Example 1. In each of Examples 15 to 17, the zeolites utilized were prepared according to the procedure of Example 8. Examples 18 to 20 employed the zeolite prepared by th general procedure given in Example 5. The zeolites of Examples 21 and 22 were prepared in accordance with Example 7. Example 23 employed a zeolite prepared by the procedure of Example 6. In Examples 24 and 25, the zeolite employed was H-Mordenite (de-aluminized H-Zeolon) having a $SiO_2/Al_2O_3$ ratio of about 61.

The aforementioned zeolites were used according to the typical experiment given herein. The results of Examples 10 to 25, which are summarized in Table 1, clearly demonstrate the superior selectivity of HZSM-5 and HZSM-11 for the sorption of paraffins over aromatics. This selectivity, which occurs preferentially at room temperature in the liquid phase, is not due to kinetic diffusional causes, as both substrates readily diffuse into the zeolite. As shown in Table 1, there is an extremely high preference of both HZSM-5 and HZSM-11 for linear paraffin n-nonane relative to the aromatic para-xylene, despite the fact that the sorption capacity for each compound if taken individually would be similar.

Although the Cs and $NH_4$ forms of ZSM-5 and ZSM-11 are not as selective as the hydrogen forms for the separation of non-aromatic linear compounds from aromatic compounds, these cation forms still exhibited better selectivity than ZSM-12 and Mordenite.

EXAMPLES 26 AND 27

Examples 26 and 27 serve to illustrate the selective separation of a non-aromatic compound, e.g. n-nonane, from a mixture thereof with an aromatic compound, e.g. para-xylenes. The zeolite to be used in Example 26 is HZSM-23 prepared as in Examples 1 and 10 of U.S. Pat. No. 4,076,842, incorporated herein by reference. The HZSM-23 exhibits a $SiO_2/Al_2O_3$ mole ratio of 60.6 and a sodium content of 0.05 weight percent. The zeolite to be used in Example 27 is HZSM-35 prepared as in Example 1 of U.S. Pat. No. 4,016,245, incorporated herein by reference, and ion-exchanged and calcined as in Examples 1 and 2 of this application. The HZSM-35 exhibits a $SiO_2/Al_2O_3$ mole ratio of 29.9.

The experiment of Example 12 is repeated with the zeolites of Examples 26 and 27 indicating selectivity of the HZSM-23 and HZSM-35 for sorption of paraffins, e.g., n-nonane, in admixture with aromatics, e.g. para-xylene. The selectivity factor in these Examples is greater than unity.

EXAMPLES 28 TO 31

These examples show the selective sorption of an olefin (heptene-1) over an aromatic (toluene).

In each of Examples 28 and 29, the zeolite employed was prepared by the general procedure of Example 2. The zeolites of Examples 30 and 31 were prepared by the general procedure of Example 7.

The aforementioned zeolites were used in conjunction with the typical experiment given in Examples 10 to 25. The results of Examples 28 to 31 clearly demonstrate the outstanding efficacy in the use of HZSM-5 to preferentially sorb an olefin over an aromatic. The results of Examples 28 to 31 are outlined in Table 2.

EXAMPLE 32

This example establishes the selective sorption of mixed paraffins from aromatics. The utility of this example is that a novel dewaxing process is now available via the selective sorption of paraffins from oils.

An Arab Light Distillate (204°–343° C.) was passed over 9 grams of a highly siliceous ZSM-5 zeolite ($SiO_2/Al_2O_3$ mole ratio of about 1670) at 250° C. in a column. Said zeolite was prepared in accordance with the general procedure of Example 9. The early fraction elutriating from the column was highly enriched in aromatics; the aromatic content increased 87.5% (based on proton n.m.r.) and the freezing point was reduced from −20° C. to −90° C.

EXAMPLE 33

The selective sorption of methyl substituted hydrocarbons vs. aromatics is clearly shown in this example.

A solution was prepared containing the following materials:

| | |
|---|---|
| 0.2 gram | 2-methylheptane |
| 0.2 gram | p-xylene |
| 0.3 gram | 1,3-di(trifluoromethyl)benzene (as internal standard) |
| 7.3 grams | 1,3,5-triisopropylbenzene(inert solvent) |

Three grams of the above solution was added to one gram of HZSM-5 prepared according to the general procedure of Example 2. At equilibrium, 63.5% of the 2-methylheptane was sorbed, whereas only 20.6% of the p-xylene was sorbed—a selectivity factor of 6.7.

EXAMPLES 34–36

In these examples, selective separations involving heteroatom substituted compounds were demonstrated. For each of these examples, the typical experimental procedure given in Examples 10–25 was followed and the zeolite utilized for all these examples was HZSM-5 prepared according to the general procedure of Example 2. The results for Examples 34–36 are given in Table 3.

TABLE 1

| | | | | | | | | Total | |
|---|---|---|---|---|---|---|---|---|---|
| Ex. No. | Zeolite | Time hrs. | Inert Solvent | n-Paraffin A | Aromatic B | % A Sorbed | % B Sorbed | Sorbed mg/g | Selectivity A/B |
| 10 | HZSM-5 | 1 | M | n-nonane | p-xylene | 98 | 17 | 55 | >200 |
| 11 | HZSM-5 | 4 | T | " | " | 72 | 3 | 56 | 82 |
| 12 | HZSM-5 | 27 | T | " | " | 74 | 4.7 | 59 | 57 |
| 13 | NH4—ZSM-5 | 4 | T | " | " | 81 | 33 | 64 | 9 |

TABLE 1-continued

SELECTIVE SORPTION OF A PARAFFIN OVER AN AROMATIC

| Ex. No. | Zeolite | Time hrs. | Inert Solvent | n-Paraffin A | Aromatic B | % A Sorbed | % B Sorbed | Total Sorbed mg/g | Selectivity A/B |
|---|---|---|---|---|---|---|---|---|---|
| 14 | NH₄—ZSM-5 | 48 | T | " | " | 84 | 32 | 65 | 11 |
| 15 | Cs—ZSM-5 | 2 | T | " | " | 89 | 52 | 65 | 8 |
| 16 | Cs—ZSM-5 | 21 | T | " | " | 91 | 52 | 66 | 9 |
| 17 | Cs—ZSM-5 | 48 | T | " | " | 91 | 52 | 66 | 9 |
| 18 | HZSM-11 | 6 | T | " | " | 98 | 34 | 66 | 99 |
| 19 | HZSM-11 | 5 | T | " | " | 77 | 3 | 60 | 116 |
| 20 | HZSM-11 | 24 | T | " | " | 78 | 4 | 61 | 83 |
| 21 | HZSM-12 | 4 | T | " | " | 27 | 30 | 43 | 0.87 |
| 22 | HZSM-12 | 24 | T | " | " | 29 | 31 | 45 | 0.90 |
| 23 | NH₄—ZSM-12 | 2 | T | " | " | 47 | 40 | 35 | 1.3 |
| 24 | Dealum. H—Zeolon | 1 | T | " | " | 46 | 42 | 22 | 1.2 |
| 25 | Dealum. H—Zeolon | 70 | T | " | " | 64 | 50 | 29 | 1.8 |

TABLE 2

SELECTIVE SORPTION OF AN OLEFIN OVER AN AROMATIC

| Ex. No. | Zeolite | Time hrs. | Inert Solvent | A Olefin | B Aromatic | % A Sorbed | % B Sorbed | Total Sorbed mg/g | Selectivity A/B |
|---|---|---|---|---|---|---|---|---|---|
| 28 | HZSM-5 | 0.7 | T | heptene-1 | toluene | 79 | 26 | 158 | 11 |
| 29 | HZSM-5 | 17 | T | " | " | 96 | 23 | 179 | 76 |
| 30 | HZSM-12 | 0.7 | T | " | " | 36 | 26 | 62 | 1.6 |
| 31 | HZSM-12 | 20 | T | " | " | 46 | 21 | 67 | 3.2 |

TABLE 3

| Example No. | Compound A | Compound B | % A Sorbed | % B Sorbed | Selectivity A/B |
|---|---|---|---|---|---|
| 34 | 1-chloro-heptane (paraffinic) | chlorobenzene (aromatic) | 76.1 | 2.5 | 7100 |
| 35 | n-butylacetate (linear) | iso-butylacetate (branched) | 86.4 | 14.0 | 39 |
| 36 | P-cresol (para) | O-cresol (ortho) | 73.0 | 48.9 | 3 |

What is claimed is:

1. A process for the selective separation of non-aromatic compounds in admixture with aromatic compounds which comprises contacting the mixture with zeolite ZSM-23 or ZSM-35, said zeolites characterized by a silica to alumina mole ratio of greater than about 12 to effect the selective sorption of said non-aromatic compounds by said zeolite.

2. The process of claim 1 wherein said zeolite has been calcined in an inert atmosphere.

3. The process of claim 2 wherein said zeolite has after calcination had its original cations replaced, at least in part, by ion exchange with a cation selected from the group consisting of hydrogen, ammonium, tetramethylammonium, rare earth metals and metals of Groups I through VIII of the Periodic Table of Elements.

4. The process of claim 3 where said zeolite has after ion exchange been calcined in an inert atmosphere.

5. The process of claim 1 wherein said zeolite has had its original cations replaced, at least in part, by ion exchange with a cation selected from the group consisting of hydrogen, ammonium, tetramethylammonium, rare earth metals and metals of Groups I through VIII of the Periodic Table of Elements.

6. The process of claim 1, 2, 3, 4 or 5 wherein said zeolite is comprised substantially of crystals of a size greater than about 0.5 micron.

7. The process of claim 1, 2, 3, 4, or 5 wherein said non-aromatic compounds are selected from the group consisting of paraffins and olefins.

8. The process of claim 1, 2, 3, 4 or 5 wherein said non-aromatic compounds are selected from the group consisting of linear paraffins, linear olefins, methyl-branched paraffins and methyl-branched olefins.

9. The process of claim 1, 2, 3, 4, or 5 wherein said aromatic compounds are benezene or alkyl-substituted benzene.

10. The process of claim 1, 2, 3, 4, or 5 wherein said alkyl-substituted benzene compounds are selected from the group consisting of toluene, ethylbenzene and xylenes.

11. The process of claim 3, 4, or 5 wherein said replacing cation is hydrogen, ammonium or tetramethylammonium.

12. The process of claim 1, 2, 3, 4, or 5 wherein the mixture is in the liquid phase.

13. The process of claim 1, 2, 3, 4, or 5 wherein the mixture is the gas phase.

14. The process of claim 1 wherein the zeolite consists essentially of HZSM-23 having a silica/alumina mole ratio of at least about 60.6, and wherein said non-aromatic compounds comprise linear paraffin and said aromatic compounds comprise xylene.

15. The process of claim 1 wherein said zeolite consists essentially of HZSM-35.

* * * * *